United States Patent
Moulder et al.

(10) Patent No.: US 7,450,995 B2
(45) Date of Patent: Nov. 11, 2008

(54) IMPLANTABLE CARDIAC STIMULATION DEVICE INCLUDING AN OUTPUT CIRCUIT THAT PROVIDES ARBITRARILY SHAPED DEFIBRILLATION WAVEFORMS

(75) Inventors: J. Christopher Moulder, Encino, CA (US); Gabriel A. Mouchawar, Valencia, CA (US); Steven W. Badelt, Granada Hills, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 567 days.

(21) Appl. No.: 10/687,386

(22) Filed: Oct. 15, 2003

(65) Prior Publication Data

US 2005/0085862 A1 Apr. 21, 2005

(51) Int. Cl.
*A61N 1/40* (2006.01)
(52) U.S. Cl. .............. 607/74; 607/4; 607/5; 607/7
(58) Field of Classification Search ............ 607/4–5, 607/7, 74
See application file for complete search history.

(56) References Cited

U.S. PATENT DOCUMENTS

| | | | | |
|---|---|---|---|---|
| 5,184,616 A | 2/1993 | Weiss | ............... | 128/419 |
| 5,470,341 A | 11/1995 | Kuehn et al. | ............... | 607/5 |
| 5,716,381 A | 2/1998 | Reggiardo | ............... | 607/8 |
| 5,725,560 A * | 3/1998 | Brink | ............... | 607/5 |
| 5,733,310 A | 3/1998 | Lopin et al. | ............... | 607/4 |
| 6,175,765 B1 | 1/2001 | Sullivan et al. | ............... | 607/5 |
| 6,208,896 B1 * | 3/2001 | Mulhauser | ............... | 607/5 |
| 6,563,377 B2 | 5/2003 | Butler | ............... | 330/10 |
| 2002/0022867 A1 * | 2/2002 | Akiyama et al. | ............... | 607/66 |
| 2003/0088281 A1 * | 5/2003 | Ostroff et al. | ............... | 607/5 |
| 2003/0125773 A1 | 7/2003 | Havel et al. | | |

* cited by examiner

*Primary Examiner*—Carl H Layno
*Assistant Examiner*—Deborah Malamud

(57) ABSTRACT

An output circuit for use in an implantable cardiac defibrillation provides an output pulse having a waveform of virtually any desired shape. The device includes a sensing circuit that senses cardiac activity. An arrhythmia detector detects fibrillation responsive to the cardiac activity signal. The device further includes an output circuit that provides a stimulation output pulse when the arrhythmia detector detects a cardiac arrhythmia. The output circuit includes an H-bridge having a pair of switching devices which control the output pulse waveform with pulse-width modulation and a second pair of switching devices that control the output pulse polarity.

6 Claims, 8 Drawing Sheets

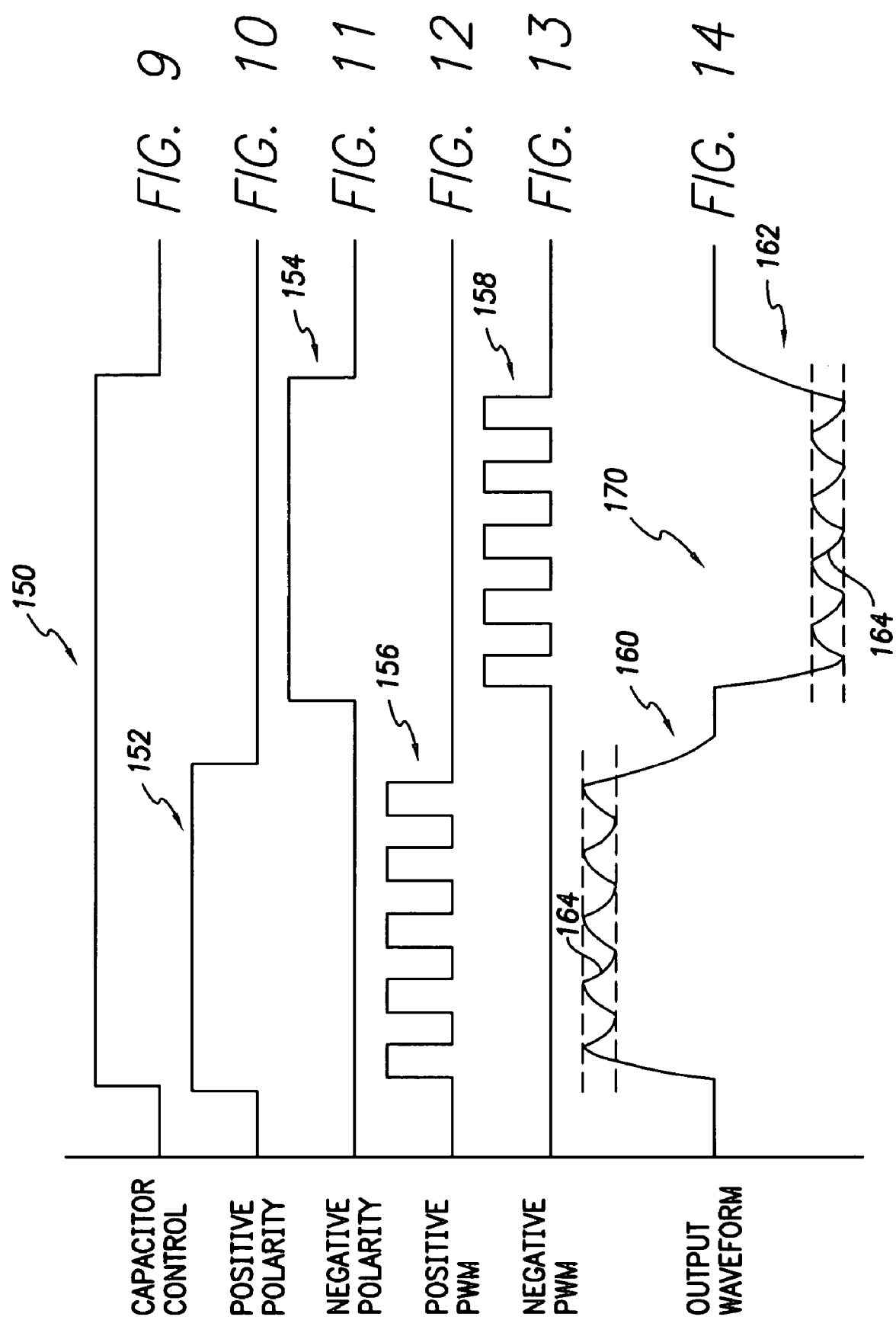

IMPLANTABLE CARDIAC STIMULATION DEVICE INCLUDING AN OUTPUT CIRCUIT THAT PROVIDES ARBITRARILY SHAPED DEFIBRILLATION WAVEFORMS

FIELD OF THE INVENTION

The present invention is generally directed to an implantable cardiac defibrillation device (ICD). The present invention is more particularly directed to such a device having an output circuit capable of providing a defibrillation pulse having a waveform of virtually any desired shape.

BACKGROUND OF THE INVENTION

Implantable cardiac defibrillators (ICD's) are well known in the art. These devices, encapsulated in a conductive housing or enclosure, are generally implanted in a pectoral region of a patient and electrically connected to the heart with one or more electrode carrying leads. One lead includes at least one defibrillation electrode arranged to be positioned in the right ventricle. An arrhythmia detector detects ventricular arrhythmias, such as ventricular fibrillation. When such an arrhythmia is detected, a pulse generator delivers a defibrillation shock pulse from the defibrillation electrode in the right ventricle to the conductive housing to terminate the arrhythmia. Alternatively, such arrhythmia terminating systems may further include another defibrillation electrode arranged to be positioned in the right atrium and electrically connected to the right ventricular defibrillation electrode. In this arrangement, the defibrillating shock is delivered from the parallel connected right ventricular and right atrial electrodes to the conductive housing.

For defibrillation therapy to be effective, the defibrillation pulse provided by the device must be at an output level above the defibrillation threshold. Implantable defibrillators generally provide a biphasic output pulse having a waveform which is shaped based upon a capacitive discharge. Such waveform shapes are generally characterized by a peak starting voltage followed by a capacitive decay. In a biphasic output, the polarity of the pulse is reversed during the duration of the output pulse.

Recently, output pulse waveform shapes, other than those based upon a capacitive discharge have been proposed and possess the potential to lower defibrillation thresholds. Since these devices are fully implantable and rely on battery power, a reduced defibrillation threshold, requiring less defibrillation pulse energy, would lead to extending the useful life of the implanted device. Further, reduced defibrillation energies also have the potential of being less traumatic to the patient.

SUMMARY

What is described herein is an output circuit for use in an implantable cardiac device which is capable of providing stimulation outputs having arbitrary waveforms previously unavailable with standard capacitive discharge devices. These waveforms offer decreased output energy requirements and the ability to tailor a stimulation output for a given patient.

In accordance with one embodiment, the output circuit may comprise a voltage supply circuit that provides an output voltage and a control circuit comprising an H-bridge that pulse-width modulates the output voltage to provide a stimulation output having a pulse-width modulated waveform.

The H-bridge may include a first leg and a second leg. Each leg may include a first switching device that controls the waveform shape of the stimulation output.

The output circuit may further include a pulse-width modulation circuit coupled to the first switching device of each leg of the H-bridge. Each leg of the H-bridge may further include a second switching device that controls polarity of the stimulation output. A polarity control circuit may be coupled to the second switching device of each leg of the H-bridge to control polarity of the output waveform. The output circuit may further include a comparison circuit that compares a desired output waveform to a timing waveform and provides control signals. The first switching may then be responsive to the control signals for creating the desired waveform.

The output circuit may further comprise a capacitor coupled between the legs of the H-bridge. The capacitor may be a non-polar capacitor.

The output circuit may further comprise an inductor coupled in series with the legs of the H-bridge. The inductor may provide additional filtering of the stimulation output.

In accordance with other aspects of the present invention, the H-bridge may comprise a plurality of legs, each leg including an output voltage modulating device. Each leg may further include a polarity control device.

The H-bridge may more particularly comprise first, second, and third legs. When the polarity control device of the first leg controls the polarity, the output voltage modulating devices of the second and third legs may independently modulate the output voltage.

In accordance with further aspects of the present invention, the invention provides an output circuit for use in an implantable cardiac device that provides a stimulation output having a desired waveform. The output circuit includes a power source that provides an output voltage, a pulse-width modulation circuit that generates a pulse-width modulation control signal corresponding to a desired waveform, and an H-bridge coupled to the power source and to the pulse-width modulation control circuit that modulates the output voltage to provide a stimulation output having the desired waveform.

BRIEF DESCRIPTION OF THE DRAWINGS

Further features and advantages of the present invention may be more readily understood by reference to the following description taken in conjunction with the accompanying drawings, in which:

FIG. 9 is a timing waveform for switching a filter capacitor in circuit in the output control circuit of FIG. 4;

FIG. 10 is a timing waveform for generating a positive going output waveform by the circuit of FIG. 4;

FIG. 11 is a timing waveform for generating a negative going output waveform by the circuit of FIG. 4;

FIG. 12 is a timing waveform of an illustrative pulse-width modulation control signal which may be employed to produce the positive going waveform;

FIG. 13 is a timing waveform of another illustrative pulse-width modulation control signal which may be employed to produce the negative going waveform;

FIG. 14 illustrates the resulting stimulation output waveform from the control signals of FIGS. 9-13;

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
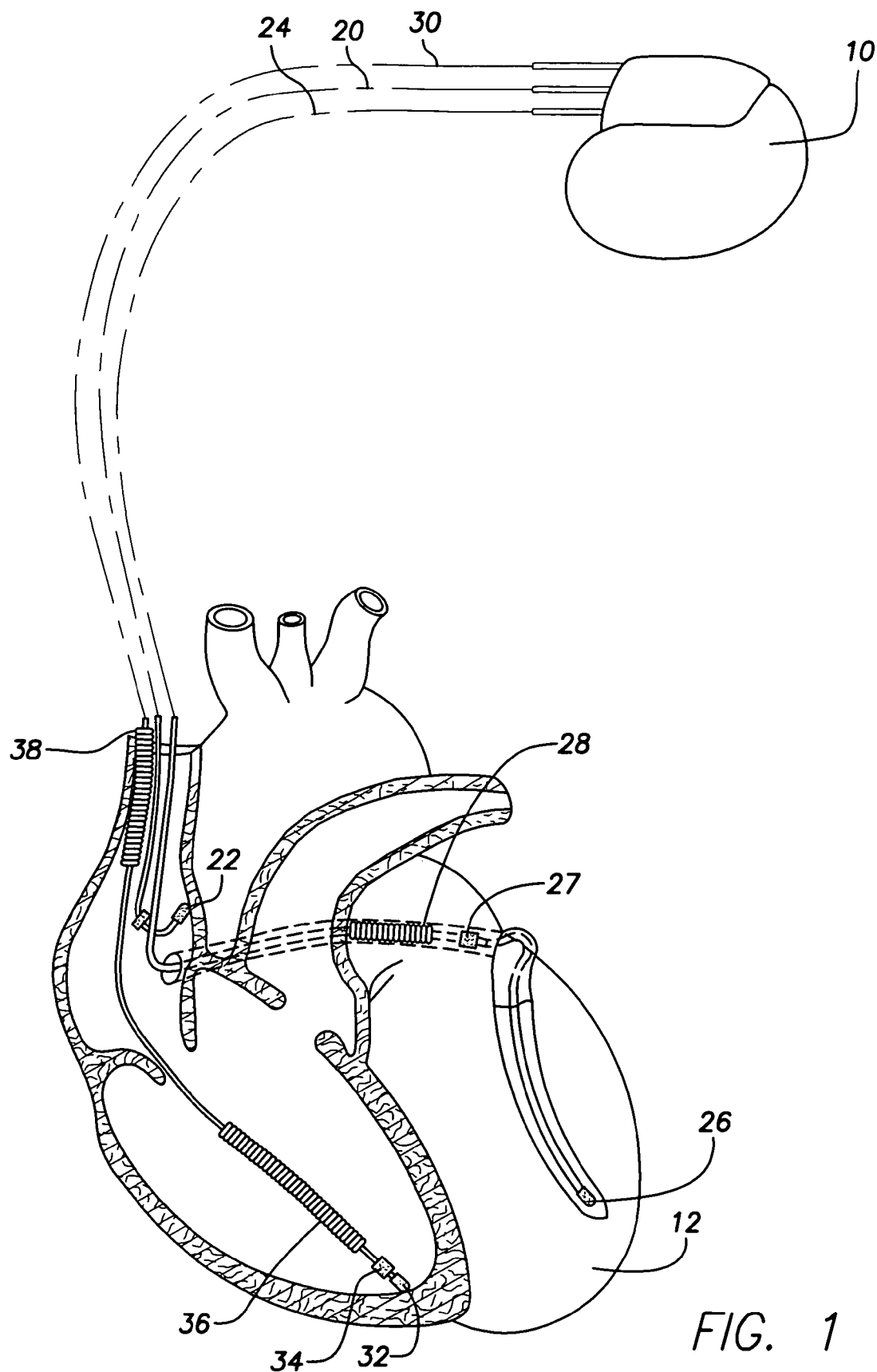
FIG. 1 is a simplified diagram illustrating an implantable stimulation device embodying the present invention in electrical communication with a patient's heart by at least three leads for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
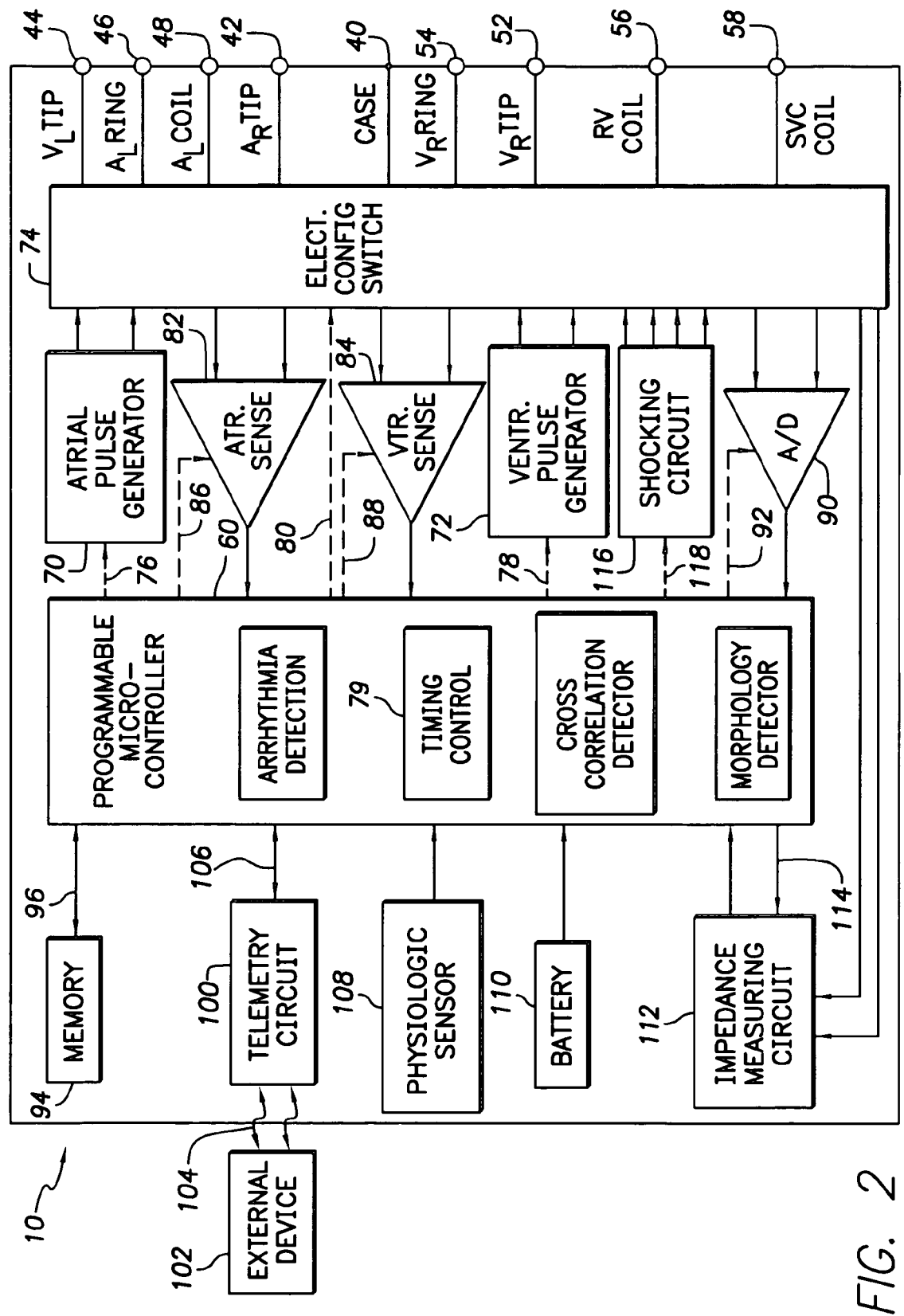
FIG. 2 is a functional block diagram of the implantable stimulation device of FIG. 1 illustrating further details thereof for providing cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a stimulation output circuit (shocking circuit) 116 by way of a control signal 118. The shocking circuit 116 will be more particularly described with respect to FIG. 3. It generates shocking pulses of low (up to 0.5 joules), moderate (0.5-10 joules), or high energy (11 to 40 joules) and of virtually any desired waveform. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
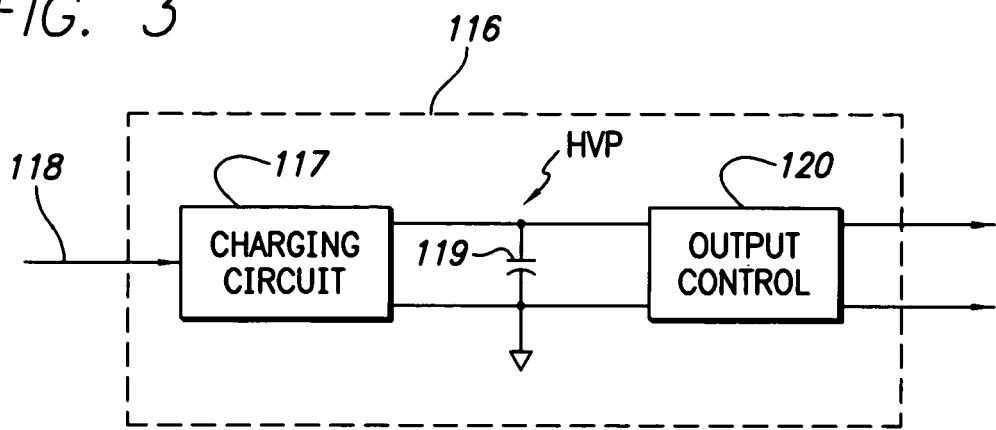
FIG. 3 is a block diagram of a stimulation output circuit embodying the present invention.

Referring now to FIG. 3, it is a block diagram of the stimulation output circuit 116 which embodies the present invention and which may be used to advantage in the implantable cardiac device 10 of FIG. 2. As will be seen subsequently, the output circuit 116 is capable of providing a stimulation output having essentially any desired waveform.

The output circuit 116 generally includes a charging circuit 117 and an output control circuit 120. The output circuit 116 further includes a high voltage capacitor 119.

The charging circuit 117 may be of a type well known in the art for charging the capacitor 119 to a desired level. Once the capacitor is charged, under control of control signal 118, an output voltage (HVP) will reside across the capacitor 119. It is this stored voltage that is modulated by the output control 120 to produce the stimulation output having the desired waveform.

Figure 4:
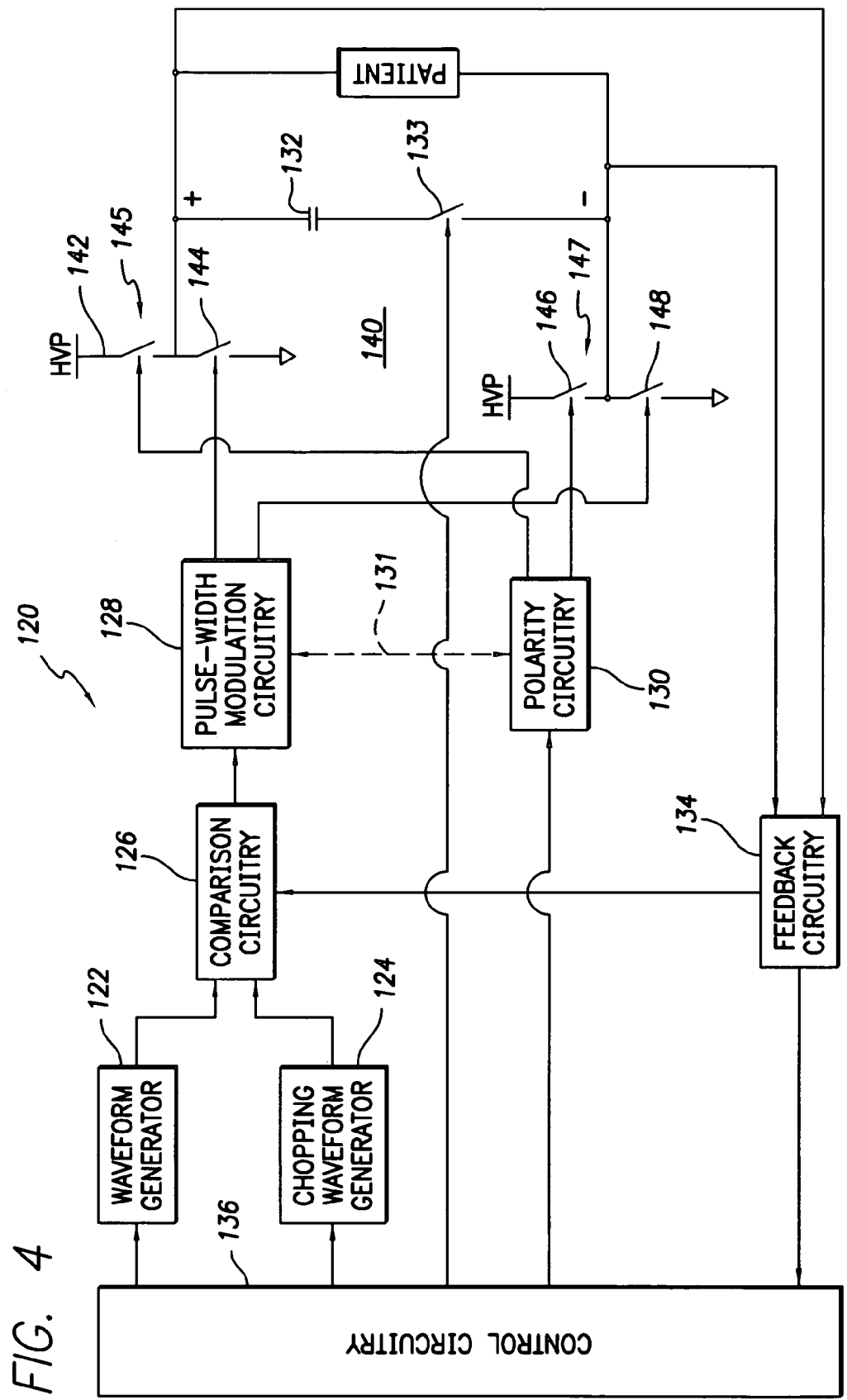
FIG. 4 is a block diagram of an output control circuit embodying the present invention.

Referring now to FIG. 4, it is a block diagram of an output control circuit which embodies the present invention and which may be used to advantage in the shocking circuit 116 of FIG. 3. As will be seen subsequently, the output control circuit 120 is capable of providing a stimulation output having a waveform of virtually any desired shape.

The control circuit 120 generally includes a waveform generator 122, a chopping waveform generator 124, a comparison circuit 126, a pulse-width modulation circuit 128, and a polarity control circuit 130. The control circuit 120 further includes an H-bridge 140, an output capacitor 132 and series switch 133, and a feedback circuit 134.

The waveform generator 122 and chopping waveform generator 124 are coupled to the comparison circuit 126. The output of the comparison circuit 126 is coupled to the pulse modulation circuit 128. A connection 131 may be made between the pulse-width modulation circuit 128 and the polarity control circuit 130 to assure that polarity is not changed when the pulse-width modulation circuit is active.

The outputs of the pulse-width modulation circuit 128 and the polarity control circuit 130 are coupled to the H-bridge 140. The H-bridge 140 includes a first leg or half 145 and a second half 147. The first half 145 includes a pair of switching devices 142 and 144. The second half 147 of the H-bridge 140 includes switching devices 146 and 148. The switching devices may be, for example, IGBT devices. Switching devices 142 and 146 control the polarity of the stimulation output and devices 144 and 148 control the waveform of the stimulation output.

The output capacitor 132 is coupled across the H-bridge 144. It in turn is coupled in parallel to the patient. The capacitor 132 is preferably a bipolar capacitor.

The feedback circuit 134 is coupled across the capacitor 132 for sensing the output pulse voltage. The output of the feedback circuit 134 is coupled to the comparison circuit 126.

Switch 133 is in series with the capacitor 132. The capacitor 132 is across the circuit output. The switch 133 may be employed for generation of a standard truncated exponential output. It also prevents charging of capacitor 132 during external defibrillation. In operation, the waveform generator 122 provides an electrical signal representing the desired waveform for the stimulation output, such as a defibrillation pulse. The chopping waveform generator 124 provides a high frequency (for example 500 kilohertz) triangle or saw-tooth waveform. The output of the comparison circuit 126 provides a control signal in response to the signals from the waveform generator 122 and the chopping waveform generator 124. The pulse-width modulation circuit 128 then provides a modulated output comprising a pulse train of pulses having varying duty cycles. The pulse-width modulation circuit further conditions the pulse train to adjust duty cycle, polarity, etc. The pulse-width modulated pulse train is coupled to switching devices 144 and 148 to control the waveform of the stimulation output. The control circuitry 136 provides a polarity control signal which is in turn provided to the polarity control circuit 130. The outputs of the polarity control circuit 130 are coupled to switching devices 142 and 146 for controlling the polarity of the defibrillation output pulse.

If the polarity is as indicated in FIG. 4, the voltage to the patient will be considered positive when switching device 142 is turned on, switching devices 144 and 146 are turned off, and when switching device 148 modulates the output voltage (HVP) to control the amplitude of the output voltage. Conversely, the voltage to the patient will be considered negative when switching device 146 is turned on, switching devices 142 and 148 are turned off, and switching device 144 modulates the output voltage to control the amplitude of the output voltage. The output amplitude is fed back to the comparison circuit 126 to adjust the pulse widths of the output based upon the desired amplification at the output. The feedback circuit 134 may, for example, be a differential amplifier.

The pulse-width modulation circuit provides further conditioning of the modulation signal. For example, it may limit duty cycle or pulse train polarity based on output polarity.

One advantage of the output circuit in accordance with the present invention is that the amplitude control devices are switched at a sufficiently high frequency such that the patient, in conjunction with capacitor 132, will act as a low pass filter. As a result, high efficiency pulse-width modulation amplification is obtained without the use of a low pass inductor. This is particularly important in as much as space and in an implanted device is at a premium and inductors are generally large in size. It may also be noted that only switching devices 144 and 148 are switched to control the waveform of the output pulse. This may serve to lower the amount of energy required to operate the H-bridge and thus save battery power.

Figure 5:
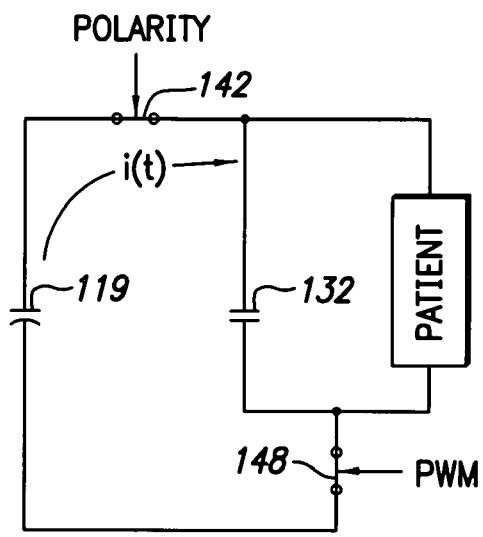
FIG. 5 is a simplified circuit diagram illustrating current flow through the patient during a first phase of pulse-width modulation.
Figure 6:
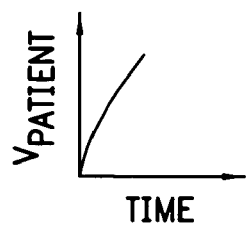
FIG. 6 is a graph illustrating the corresponding voltage waveform generated during the first phase of pulse-width modulation.

Referring now to FIGS. 5 and 6, they illustrate the current flow and resulting output voltage when the control circuit 120 is in a first phase of the pulse-width modulation. The first phase is when the polarity switch 142 is closed along with the modulating switch 148. When both switches 142 and 148 are closed, current flows from the high voltage storage capacitor 112 into the patient and filter capacitor 132. As may be best seen in FIG. 6, the voltage across the patient rises at a rate determined by the capacitance value of the filter capacitor 132 and the impedance of the patient.

Figure 7:
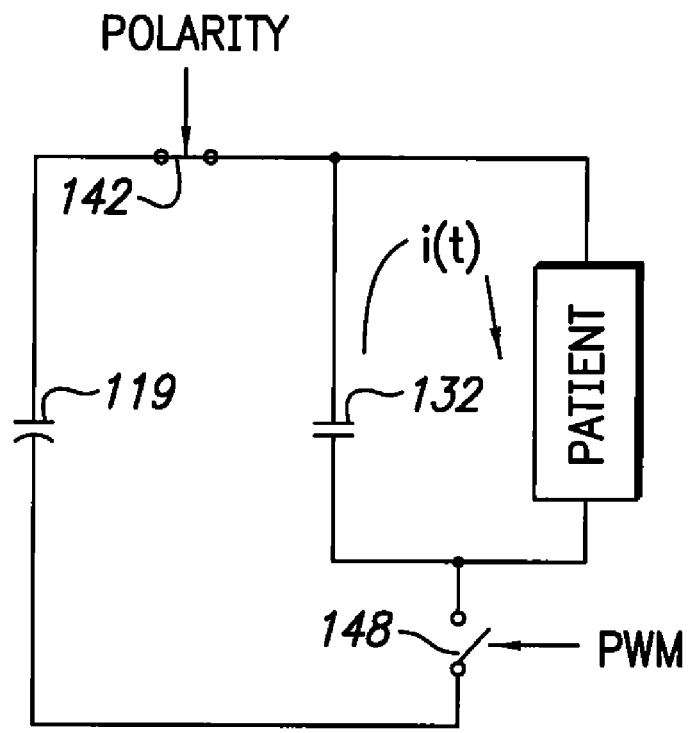
FIG. 7 is a simplified circuit diagram illustrating current flow through the patient during a second phase of pulse-width modulation.
Figure 8:
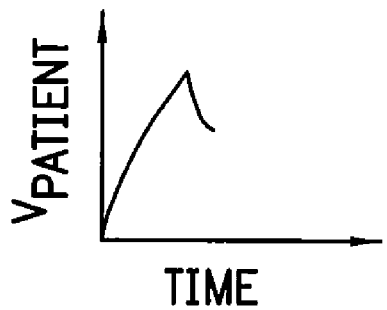
FIG. 8 is a graph illustrating the corresponding voltage waveform generated during the second phase of pulse-width modulation.

As may be seen in FIG. 7, when switch 148 is switched open, current ceases to flow from the high voltage capacitor 119 and instead is sourced by the filter capacitor 132. Hence, as will be noted in FIG. 8, the voltage across the patient decreases at a rate determined by the capacitance value of capacitor 132 and the impedance of the patient.

FIGS. 9-14 provide an illustrative example of how a stimulation output having a desired waveform may be provided by the control circuit 120. When the stimulation output is to be provided, control signal 150 is provided by the control circuitry to close the series switch 133. The series switch 133 remains closed throughout the provision of the stimulation output.

FIG. 10 shows control signal 152 which causes polarity switch 142 to close for providing a positive going waveform portion of the stimulation output. While polarity switch 142 is closed, a pulse-width modulation pulse train 156 as illustrated in FIG. 12 is provided to the modulation switch 148. The result is a positive going portion 160 of the stimulation output 170 illustrated in FIG. 14. When the positive going portion of the stimulation output is to terminate, the polarity switch 142 opens and a control signal 154 shown in FIG. 11 causes polarity switch 146 to close. With polarity switch 146 closed, the post width modulation circuitry provides another pulse train 158 illustrated in FIG. 13 to control the modulation switch 144. This results in a negative going portion 162 of the stimulation output waveform 170.

The foregoing illustrates the provision of a stimulation output having a 50% duty cycle. As will be appreciated by those skilled in the art, this is but a simplified example of the many different kinds of waveforms which may be generated in accordance with the present invention.

Figure 15:
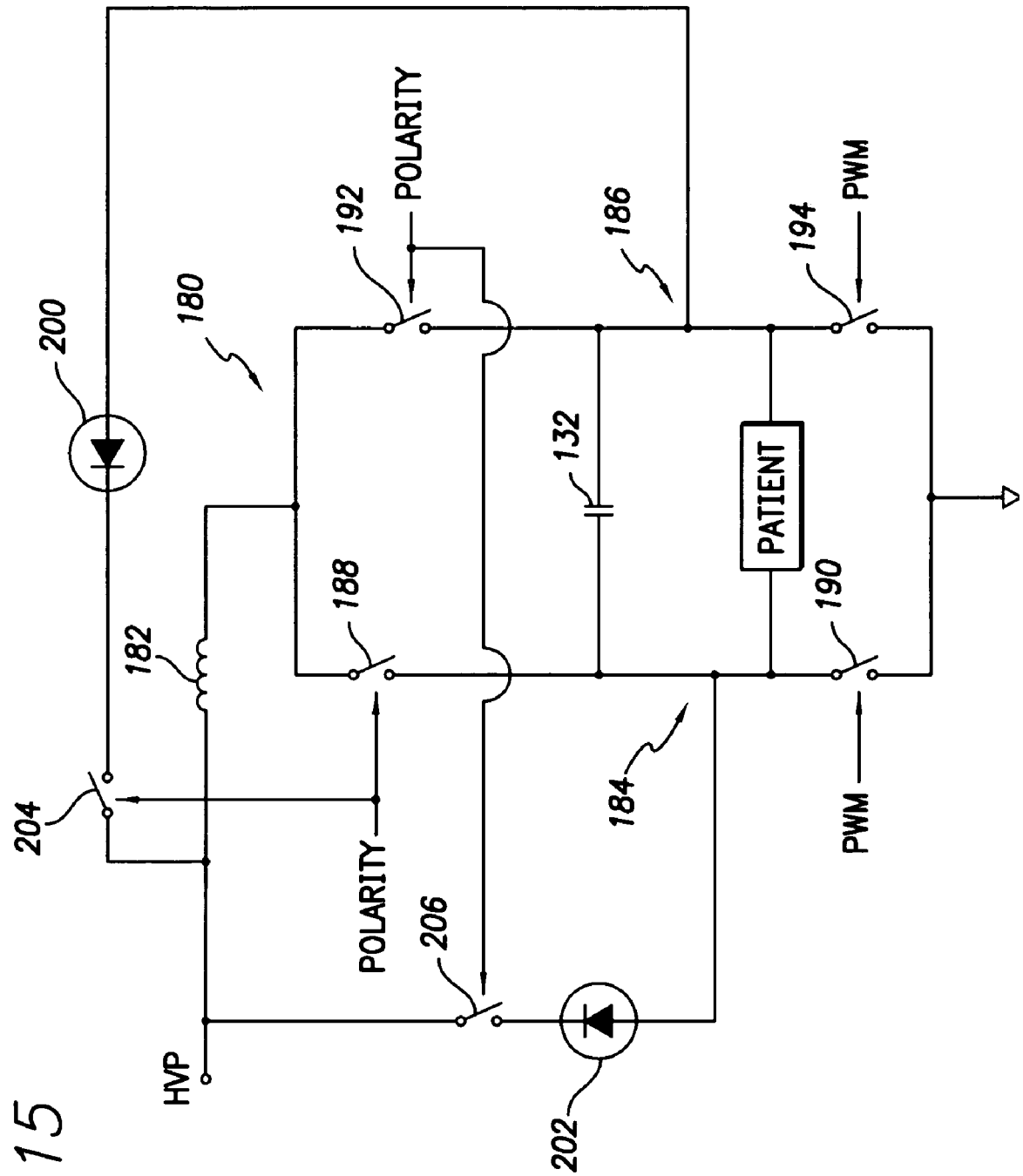
FIG. 15 is a circuit diagram illustrating an H-bridge which may be employed to advantage in accordance with a further embodiment of the present invention.

As will be noted in FIG. 14, the output waveform 170 exhibits a slight ripple 164 due to the finite capacitance of capacitor 132 and finite impedance of the patient. In FIG. 15, an H-bridge 180 is illustrated which provides for greater filtering of the output waveform to greatly eliminate the aforementioned ripple in the output waveform. To this end, the H-bridge 180 includes a series inductor 182 which is coupled in series with the legs or bridge halves 184 and 186 of the H-bridge 180. As will be noted, leg 184 includes a polarity control switching device 188 and a pulse-width modulating switching device 190. Similarly, leg 186 includes a polarity switching device 192 and a pulse-width modulating device 194. Coupled between the legs 184 and 186 is the filter capacitor 132. In use, the H-bridge is coupled to the patient such that the filter capacitor 132 is in parallel connection with the patient as in the previous embodiment of FIG. 4.

The H-bridge 180 further includes blocking diodes 200 and 202. Blocking diode 200 is switched in circuit by a switch 204 which closes when polarity switch 188 closes. Similarly, blocking diode 202 is switched in circuit by a switch 206 when polarity switch 192 is closed.

The operation of the H-bridge 180 is identical to the operation of the H-bridge 140 of FIG. 4. The added inductor 182 serve to provide greater filtering of the output waveform for eliminating the ripple 164 as may be seen in FIG. 14.

Figure 16:
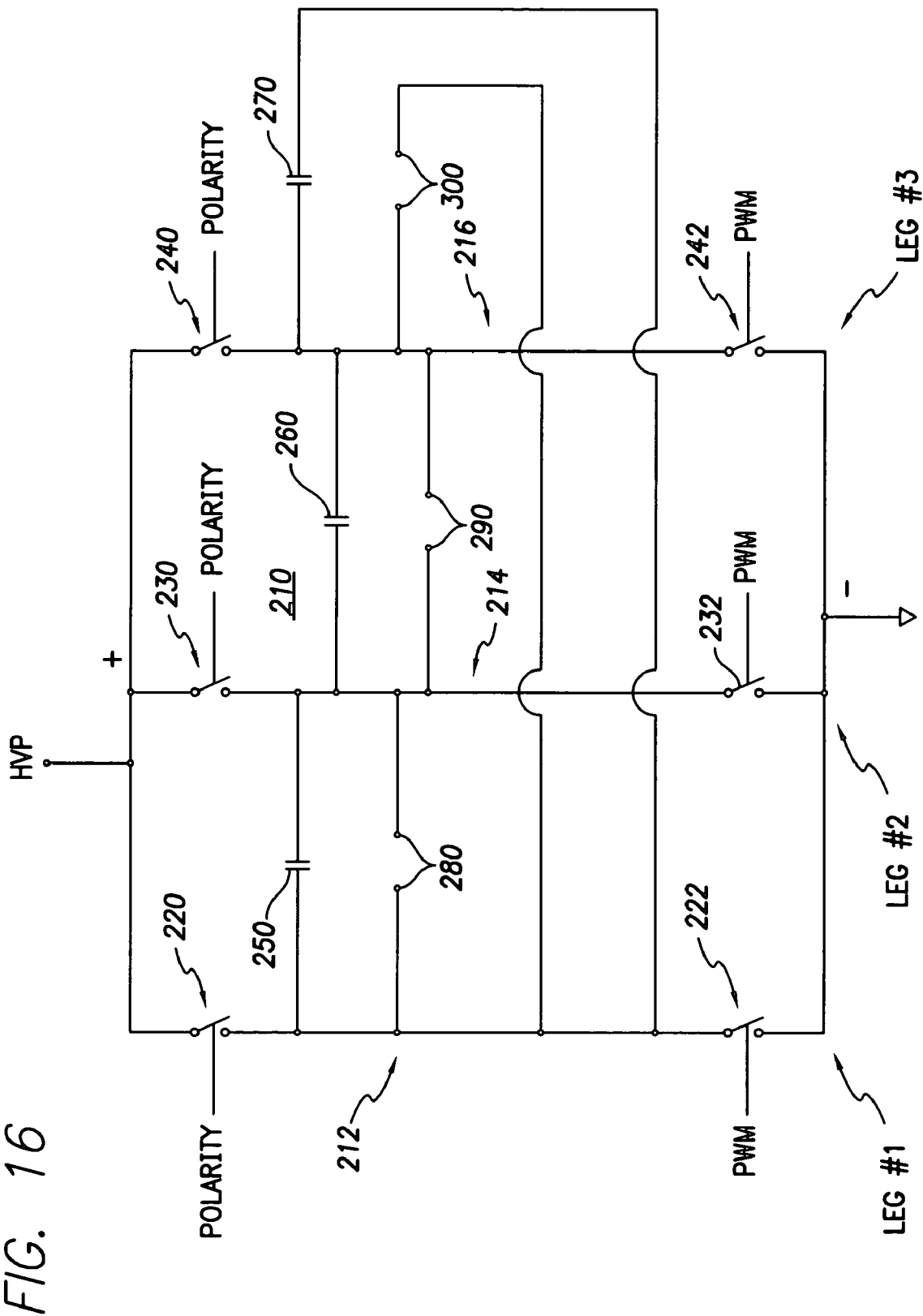
FIG. 16 is a circuit diagram of a still further H-bridge embodying the present invention.

Referring now to FIG. 16, it illustrates another H-bridge 210 embodying the present invention. The H-bridge 210 includes bridge halves, or legs, 212, 214, and 216. Leg 212 includes polarity control switch 220 and modulating switch 222. Leg 214 includes polarity switch 230 and modulating switch 232. Similarly, leg 216 includes polarity switch 240 and modulating switch 242. Coupled across adjacent legs is a filter capacitor. Hence, filter capacitor 250 is coupled between legs 212 and 214, filter capacitor 260 is coupled between leg 214 and 216, and filter capacitor 270 is coupled between leg 216 and 212. Across the filter capacitors are outputs 280, 290, and 300. The outputs may be connected to the electronic configuration switch 74 (FIG. 2) such that the outputs may be coupled to different stimulation vectors as may be known in the art.

The H-bridge 210 of FIG. 16 has the advantage that, for a positive polarity as indicated in the figure, when the polarity control switch of one of the legs is closed, the output voltage modulating switches of the other two legs are configured to independently modulate the output voltage. Hence, for example, if switch 220 is closed, switches 232 and 242 may be operating independent of one another for controlling the waveform of the stimulation output. This provides for a further degree of flexibility in providing a desired waveform. Similarly, if polarity switch 230 is closed, modulating switches 222 and 242 may be operating independently to modulate the stimulation output and if polarity switch 240 is closed, modulating switches 222 and 232 may be operated independently to modulate the output.

Still further, if it is desired to modulate the output in this manner for a negative going output waveform portion, any one of the pulse-width modulation switches may be closed and the polarity switches of the other two legs may be operated independently to control the output waveform. As a result, the H-bridge 210 of FIG. 16 provides improved flexibility towards providing a stimulation output having a desired waveform.

While the invention has been described by means of specific embodiments and applications thereof, it is understood that numerous modifications and variations may be made thereto by those skilled in the art without departing from the spirit and scope of the invention. For example, the switching devices may be field effect transistors (FETs). In addition, the chopping waveform may be eliminated and the feedback could be compared directly with the desired output waveform. It is therefore to be understood that within the scope of the claims, the invention may be practiced otherwise than as specifically described herein.

What is claimed is:

1. An output circuit for use in an implantable cardiac device comprising:
   an output adapted for connection across a load;
   a charging circuit;
   a first capacitor switchably coupled between the charging circuit and the output;
   a second capacitor switchably coupled across the first capacitor and the output;
   a pulse-width modulation circuit that generates first and second pulse-width modulation control signals;
   a polarity control circuit that generates first and second polarity control signals;
   an H-bridge including a first leg and a second leg, each leg including a pulse-width modulation switch and a polarity switch, wherein:
      the pulse-width modulation switches are configured to receive a respective one of the first and second pulse-width modulation control signals, and alternately switch between a closed state and an open state in response to the pulse-width modulation control signal; and the polarity switches are configured to receive a respective one of the first and second polarity control signals and switch between a closed state and an open state in response to the polarity control signal; and a controller programmed to:

control the polarity control circuit to generate first and second polarity control signals whereby the polarity switch of the first leg is closed and the polarity switch of the second leg is open, and control the pulse-width modulation circuit to generate first and second pulse-width modulation control signals whereby the pulse width modulation switch of the first leg is open and the pulse width modulation switch of the second leg is closed, and the first capacitor is thereby electrically coupled across the second capacitor and the output in a first polarity; and while the first capacitor is electrically coupled across the second capacitor and the output in the first polarity, further control the pulse-width modulation circuit to generate pulse-width modulation control signals whereby the pulse width modulation switch of the second leg is toggled between open, whereby the first capacitor is electrically decoupled across the second capacitor and the output, and the second capacitor is electrically coupled across the output, and closed, whereby the first capacitor is electrically coupled across the second capacitor and the output.

2. The output circuit of claim 1 wherein the second capacitor is arranged to receive current from the first capacitor when the first capacitor is electrically coupled across the second capacitor and the output and to supply current to the output when the first capacitor is electrically decoupled across the output.

3. The output circuit of claim 2 wherein the second capacitor is a non-polar capacitor.

4. The output circuit of claim 1 wherein the second pulse-width modulation control signal comprises a pulse train of pulses for toggling the pulse width modulation switch of the second leg between open and closed.

5. The output circuit of claim 4 wherein the pulses having varying duty cycles.

6. The output circuit of claim 1 wherein the controller is further programmed to:

control the polarity control circuit to generate first and second polarity control signals whereby the polarity switch of the first leg is open and the polarity switch of the second leg is closed, and control the pulse-width modulation circuit to generate first and second pulse-width modulation control signals whereby the pulse width modulation switch of the first leg is closed and the pulse width modulation switch of the second leg is open, and the first capacitor is thereby electrically coupled across the second capacitor and the output in a second polarity different from the first polarity; and while the first capacitor is electrically coupled across the second capacitor and the output in the second polarity, further control the pulse-width modulation circuit to generate pulse-width modulation control signals whereby the pulse width modulation switch of the first leg is toggled between open, whereby the first capacitor is electrically decoupled across the second capacitor and the output, and the second capacitor is electrically coupled across the output, and closed, whereby the first capacitor is electrically coupled across the second capacitor and the output.

* * * * *